United States Patent
Biber (10) Patent No.: US 11,226,632 B2
(45) Date of Patent: Jan. 18, 2022

(54) APPARATUS AND METHOD FOR COMPUTER CONTROL OF A PATIENT SUPPORT DEVICE USING AN ENVIRONMENTAL PARAMETER

(71) Applicant: Siemens Healthcare GmbH, Erlangen (DE)

(72) Inventor: Stephan Biber, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 923 days.

(21) Appl. No.: 15/977,017

(22) Filed: May 11, 2018

(65) Prior Publication Data

US 2018/0329422 A1 Nov. 15, 2018

(30) Foreign Application Priority Data

May 12, 2017 (EP) .................................. 17170786

(51) Int. Cl.
| | |
|---|---|
| *G05D 1/02* | (2020.01) |
| *A61B 5/055* | (2006.01) |
| *A61B 6/04* | (2006.01) |
| *A61G 7/018* | (2006.01) |
| *A61G 1/02* | (2006.01) |
| *A61G 7/08* | (2006.01) |
| *G05D 1/00* | (2006.01) |

(52) U.S. Cl.
CPC .......... *G05D 1/0225* (2013.01); *A61B 5/055* (2013.01); *A61B 6/0407* (2013.01); *A61B 6/0487* (2020.08); *A61G 1/0275* (2013.01); *A61G 7/018* (2013.01); *A61G 7/08* (2013.01); *G05D 1/0088* (2013.01); *G05D 1/0259* (2013.01); *A61G 2203/22* (2013.01); *A61G 2203/30* (2013.01); *A61G 2210/50* (2013.01); *G05D 2201/0206* (2013.01)

(58) Field of Classification Search
CPC .. G05D 1/0225; G05D 1/0088; G05D 1/0259; A61B 5/055; A61B 6/0407; A61B 6/0487; A61G 1/0275; A61G 7/018; A61G 7/08; A61G 2203/22; A61G 2203/30; A61G 2210/50
USPC ........................ 5/601, 600; 378/208, 209, 20
See application file for complete search history.

(56) References Cited

U.S. PATENT DOCUMENTS

| | | | | |
|---|---|---|---|---|
| 5,733,247 A | * | 3/1998 | Fallon | A61B 5/0017 324/309 |
| 8,000,770 B2 | * | 8/2011 | Schmitt | A61B 5/055 600/415 |
| 8,217,654 B2 | * | 7/2012 | Biber | G01R 33/3692 324/318 |

(Continued)

FOREIGN PATENT DOCUMENTS

| | | |
|---|---|---|
| DE | 10 2006 032798 A1 | 1/2008 |
| DE | 10 2013 208610 A1 | 11/2014 |
| DE | 10 2013 213213 A1 | 1/2015 |

*Primary Examiner* — Robert G Santos
(74) *Attorney, Agent, or Firm* — Schiff Hardin LLP (57) ABSTRACT

A patient support device has a bed, a travel mechanism designed to move the patient support device, a control computer and a sensor, which detects at least one environmental parameter of the patient support device. The control computer ascertains a control parameter for controlling the travel mechanism depending on the at least one detected environmental parameter.

18 Claims, 4 Drawing Sheets

(56) References Cited

U.S. PATENT DOCUMENTS

| | | | |
|---|---|---|---|
| 8,415,949 B2* | 4/2013 | Biber | G01R 33/341 |
| | | | 324/307 |
| 9,591,969 B2* | 3/2017 | Gross | A61B 5/062 |
| 9,662,254 B2* | 5/2017 | Haider | A61G 7/0528 |
| 10,393,829 B2* | 8/2019 | Ludwig | G01R 33/443 |
| 10,545,201 B2* | 1/2020 | Hetz | G01R 33/0023 |
| 2008/0015431 A1 | 1/2008 | Schmitt | |
| 2010/0176809 A1* | 7/2010 | Biber | G01R 33/3692 |
| | | | 324/309 |
| 2010/0289492 A1 | 11/2010 | Biber et al. | |
| 2011/0154569 A1 | 6/2011 | Wiggers et al. | |
| 2014/0088404 A1 | 3/2014 | Gross | |
| 2014/0331406 A1 | 11/2014 | Haider et al. | |
| 2015/0007390 A1 | 1/2015 | Haider et al. | |
| 2015/0374567 A1 | 12/2015 | Haider | |
| 2017/0248665 A1 | 8/2017 | Ludwig et al. | |
| 2018/0231622 A1* | 8/2018 | Hetz | G01R 33/307 |
| 2018/0329422 A1* | 11/2018 | Biber | A61G 7/08 |

* cited by examiner

APPARATUS AND METHOD FOR COMPUTER CONTROL OF A PATIENT SUPPORT DEVICE USING AN ENVIRONMENTAL PARAMETER

BACKGROUND OF THE INVENTION

Field of the Invention

The present invention concerns a patient support device with a bed, a travel mechanism designed to move the patient support device, a control computer and a sensor. Furthermore, the present invention relates to a magnetic resonance apparatus with such a patient support device and a method for controlling a travel mechanism of such a patient support device with a control computer.

Description of the Prior Art

Patient support device having docking capability must first be docked with the magnetic resonance scanner for use with the magnetic resonance scanner. Conventionally, the process of docking the patient support device has been performed largely manually, for example, by a medical technician. The technician must drive and/or push the patient support device to the magnetic resonance scanner and mate with the docking unit of the magnetic resonance scanner as precisely as possible. Depending on the experience of the user, however, this can take some time.

A patient support device that can be docked is known, for example, from DE 10 2014 212 202 and from DE 10 2012 217 634.

SUMMARY OF THE INVENTION

An object of the present invention is to enable at least partially automatic driving and/or docking of a patient support device.

The invention is based on a patient support device with a bed, a travel mechanism designed to move the patient support device, a control computer and a sensor.

In accordance with the present invention, the sensor detects at least one environmental parameter of the patient support device and, depending on the at least one environmental parameter, the control computer ascertains a control parameter for controlling the travel mechanism and emits a control signal corresponding thereto to the travel mechanism.

The patient support device can be docked to a magnetic resonance apparatus. For this purpose, the patient support device also has a docking unit situated in the direction of a direction of movement on a front side of the patient support device. The docking unit of the patient support device is preferably designed to mate with a docking unit of the magnetic resonance scanner. On the rear side of the patient support device, the patient support device preferably has an operating unit, in particular a handle via which a user can transfer a force for moving the patient support device to the patient support device.

The bed is designed to accommodate the patient thereon. In addition, the bed can be driven in a horizontal direction, in particular in the direction of a longitudinal direction of the bed, such that the bed can be inserted or moved into a patient reception area of the magnetic resonance scanner after docking of the patient support device with the magnetic resonance scanner. In addition, the bed can be designed to move a vertical direction for height adjustment. This can facilitate positioning of a patient on the bed.

The travel mechanism preferably has a number of rolling elements and/or rolling bodies such as wheels, by which the patient support device can be moved (driven). The travel mechanism preferably has four or five rolling elements and/or rolling bodies. In addition, the travel mechanism may have a drive unit that drives the rolling elements during the movement of the patient support device. By operation of the travel mechanism, the patient support device is designed to be movable in an undocked state. In the undocked state, the patient support device is not docked to the magnetic resonance scanner.

The sensor detects an environmental parameter of the patient support device. The environmental parameter may be a magnetic field strength and/or a value of a $B_0$ field generated by a superconducting basic field magnet of the magnetic resonance scanner at the location of the patient support device. Thus, with the sensor, the magnetic field strength of a static magnetic field of the superconducting basic field magnet of the magnetic resonance scanner is detected at the location of the patient support device. The static magnetic field is most homogenous in an isocenter and/or an area of examination of the magnetic resonance scanner. Outside the isocenter or the area of examination, however, the magnetic field varies greatly spatially, depending on the distance from the isocenter and/or the area of examination of the magnetic resonance scanner. If, for example, the patient support device is in the vicinity of the magnetic resonance scanner, an environmental parameter with a high magnetic field strength can therefore be detected by the sensor. If instead, the patient support device is at a distance from the magnetic resonance scanner, such as outside the range of the magnetic field generated by the magnetic resonance scanner, an environmental parameter with a low and/or non-existent magnetic field strength can be detected by the sensor.

Alternatively, or in addition, the environmental parameter may be the value of a $B_1$ field of the magnetic resonance scanner at the location of the patient support device. The value of the $B_1$ field can be detected by the sensor. Furthermore, the environmental parameter may be a value of the gradient field of the magnetic resonance scanner at the location of the patient support device. The value of the gradient field can be detected by the sensor. The environmental parameter may also be a value and/or a number of light markings that are emitted by the magnetic resonance scanner at the location of the patient support device, with the number of light markings being detected by the sensor.

When the environmental parameter is the value of a magnetic field strength, it may also include position information, the position information being dependent on the detected value of the magnetic field strength and/or the detected value of the $B_0$ field. When the environmental parameter is the value of the $B_1$ field or the value of the gradient field or a number of light markings, an item of position information can be ascertained or generated depending on the $B_1$ field or the gradient field or the number of light markings. The position information preferably represents the position of the patient support device and/or the sensor of the patient support device with respect to the magnetic resonance scanner. For example, the control computer can access a number of field maps of various magnets so that, by a comparison of the detected environmental parameter with the field maps, the magnet type of the magnetic resonance scanner can be ascertained. With the use of the selected field map, the position of the patient support device in relation to the magnetic resonance scanner can be ascertained with particular ease and precision.

The control computer preferably has an arithmetic processor. Furthermore, the control computer has control programs or control software for controlling the patient support device. For example, the control can be at least partially control of a movement of the bed in a horizontal direction and/or in a vertical direction. In addition, the control may also at least partially include control of the travel mechanism, in particular the drive unit of the travel mechanism. Furthermore, the control may be control of a direction of movement of the patient support device. Preferably, the control parameter for controlling the travel mechanism is a parameter for activating the drive unit of the travel mechanism or a parameter for adjusting the direction of movement to the rolling elements of the travel mechanism.

To determine the position depending on the environmental parameter, such as the value of a magnetic field strength, reference is made to DE 10 2009 021 026.

The invention has the advantage that the user can receive advantageous support at least during a docking procedure of the patient support device with the magnetic resonance scanner by control of the travel mechanism with the use of the control parameter by the control computer. In particular, the patient support device can be at least partially controlled in this way with the use of control parameters if the patient support device is arranged in close proximity to the magnetic resonance scanner because then a meaningful environmental parameter can be detected or is available, which also changes with a position change of the patient support device in relation to the magnetic resonance scanner. If the patient support device is at a large distance from the magnetic resonance scanner, changes to the distance and/or a position change of the patient support device in relation to the magnetic resonance apparatus are scarcely noticeable in the detected environmental parameter.

In an embodiment of the invention, the sensor has at least one environmental sensor that is a $B_0$ field sensor for detecting the $B_0$ field. The at least one $B_0$ field sensor preferably is a Hall effect sensor. A sensor designed in this way has the advantage of being particularly economical sensor for detecting the at least one environmental parameter. The $B_0$ field sensor may be a 1D field sensor, but preferably is a 2D field sensor. More advantageously, the $B_0$ field sensor is a 3D field sensor. The resulting environmental parameter detected by the $B_0$ field sensor may relate to the magnitude of the static magnetic field, such as by combining a number of Hall effect sensors arranged in different, non-parallel planes so that the surface normal of the planes spans a 3-dimensional area. The detected environmental parameter may also represent the strength of a component in a predetermined direction. The direction can be defined by the arrangement of the $B_0$ field sensor on the patient support device.

In an alternative embodiment of the invention, the sensor may have at least one $B_0$ field sensor having an embodiment deviating from a Hall effect sensor. In an alternative embodiment of the invention, the at least one environmental sensor may also have a magnetic field sensor that detects a $B_1$ field and/or a gradient field, or a light sensor.

In a preferred embodiment of the invention, the patient support device has a front area with a docking unit, wherein the docking unit is designed for docking with the magnetic resonance scanner, and the sensor is situated in the front area. Position information can be provided and/or ascertained with the use of the environmental parameter for that area of the patient support device for which particularly precise positioning is necessary for docking with the magnetic resonance scanner.

Furthermore, the sensor can have at least two environmental sensors that are arranged at a distance from one another. This enables particularly precise and accurate detection of the environmental parameter by the at least two environmental sensors. A high degree of precision and/or clarity of the detected measured values can be achieved by use of the at least two environmental sensors. As used herein, "arranged at a distance" means that the at least two environmental sensors are distributed on the patient support device from one another.

In a further embodiment of the invention, the sensor has at least one environmental sensor situated inside the bed. In this way, it can be ensured that the at least one environmental sensor, such as the at least one $B_0$ field sensor, is at a maximum distance from a floor and/or substrate on which the patient support device is movably arranged. Such a floor and/or substrate may, for example, have an iron reinforcement that can lead to a local $B_0$ distortion, and thus can lead to falsified results.

Furthermore, the patient support device can have a user interface designed for adjustment of a threshold value of the environmental parameter, wherein the threshold value specifies a criterion for the environmental parameter to ascertain the control parameter for controlling the travel mechanism with the control computer. Preferably, the threshold value of the environmental parameter is entered manually by a user. When transporting the patient support device, safety can be advantageously increased by the threshold value by, for example, automatic control of the travel mechanism of the patient support device being permitted to take place only the threshold value is reached and/or exceeded by the detected environmental parameter. Thus, for example, it is possible to prevent the control computer from already beginning to control the travel mechanism when the patient support device is still outside the examination room, and there is therefore a wall between the patient support device and the magnetic resonance scanner. A lower limit of the threshold value can be specified, this lower limit being preset as a threshold value. Therefore, when entering the threshold value, the user could increase the threshold value to a desired value.

In another embodiment of the invention, the control computer has a communication interface for communication with the magnetic resonance scanner. Preferably, the communication interface includes a data interface, in particular a cable-free or wireless data interface such as a radio interface. Via the communication interface, information can be exchanged between the control computer of the patient support device and the magnetic resonance scanner, for example, a system controller of the magnetic resonance scanner. For example, information about the design of the magnet and/or about a stray field of the magnet of the magnetic resonance scanner can be transmitted to the control computer of the patient support device. Through the exchange of such information, a particularly rapid determination of the position of the patient support device in relation to the magnetic resonance apparatus can be achieved because, as already through the transmission of such information, a typical magnet field map inside the control computer was selected and/or a typical magnet stray field is available inside the control computer. Based on this, depending on the detected environmental parameter, the patient support device can be moved.

The invention also encompasses a magnetic resonance apparatus with a patient support device, wherein the patient support device has a bed, a travel mechanism designed to move the patient support device, a control computer and a sensor, wherein the sensor detects at least one environmental parameter of the patient support device and, depending on the at least one environmental parameter, the control computer ascertains a control parameter for controlling the travel mechanism.

Preferably, the magnetic resonance apparatus also has a scanner with a docking unit designed to dock the patient support device with the scanner. The docking unit of the scanner mates with the docking unit of the patient support device. Furthermore, the scanner has a patient reception area shaped to receive a patient during a magnetic resonance scan. The patient is introduced into the patient reception area by the patient support device, by the bed of the patient support device being movable inside the patient reception area. The patient reception area is surrounded cylindrically by the scanner, in particular by the superconducting basic field magnet, the gradient coil arrangement and the radio-frequency antenna of the scanner.

The advantages of the magnetic resonance apparatus according to the invention essentially correspond to the advantages of the patient support device according to the invention as explained in detail above. Features, advantages and alternative embodiments mentioned above apply to the apparatus as well.

Furthermore, the invention encompasses a method for controlling a travel mechanism of a patient support device with a control computer that includes the following steps.

At least one environmental parameter of the patient support device is detected with a sensor, and is provided to a computer.

At least one control parameter for activating the travel mechanism is determined by the control computer, depending on the at least one environmental parameter.

The travel mechanism is activated according to the determined control parameter by the control computer.

The invention has the advantage that the user can receive assistance at least during a docking procedure of the patient support device with the magnetic resonance scanner by control of the travel mechanism with the use of the control parameter by the control computer. In this way the patient support device can be at least partially controlled with the use of control parameters, if the patient support device is arranged in the vicinity of the magnetic resonance scanner, because then a meaningful environmental parameter can be detected and made available, which also changes with a change in the position of the patient support device in relation to the magnetic resonance scanner.

The advantages of the method according to the invention essentially correspond to the advantages of the patient support device according to the invention that have been explained above. Features, advantages and alternative embodiments mentioned above apply to the method as well.

In another embodiment of the method according to the invention, the environmental parameter is a value of the $B_0$ field and/or a value of a gradient field and/or a value of the $B_1$ field and/or a number of light markings at the location of the patient support device. The value of the $B_0$ field and/or the value of a gradient field and/or the value of the $B_1$ field and/or the number of light markings, is/are preferably dependent on the position or the location of the patient support device in relation to the magnetic resonance apparatus. In this way, the position of the patient support device in relation to the magnetic resonance apparatus can be ascertained with particular ease with the use of the detected environmental parameter. For example, with the use of field maps of the basic field magnet of the scanner that are stored or deposited in the control computer of the patient support device, the spatial distribution of the magnetic field can be accessed, permitting a simple assignment of the ascertained environmental parameter to a position of the patient support device within that magnetic field. Such a field map may alternatively show a distribution or arrangement of light markings on the scanner and their visibility depending on a position or orientation of the patient support device in relation to the scanner. A field map showing respective spatial distributions of more than one type of environmental parameter, combined in one field map, are also possible.

In a further embodiment of the invention, with the use of the environmental parameter and with the use of at least one field map, the control computer determines the position of the patient support device in relation to the scanner. Preferably the at least one field map is stored or deposited in a memory associated with the patient support device, in particular, a memory of the control computer. Preferably, multiple field maps of different magnets and/or magnet types of the scanner are stored. A field map is selected from the multiple field maps by a comparison of the detected environmental parameter with each individual field map. The field maps each represent a spatial distribution of the magnetic field for a defined magnet or magnet type. Alternatively, a field map for the magnet or magnet type in the scanner to which the patient support device is to be docked can be transferred via a communication interface of the control computer from that scanner to the control computer.

With the use of the field map and the environmental parameter, the position of the patient support device in relation to the scanner can be determined expeditiously and with particular ease by the control computer. For example, the side of the scanner toward which the patient support device is being moved, or whether the patient support device is in front of or behind or to the side of the scanner, can also be determined by the control computer. Alternatively or in addition, the direction of movement of the patient support device in relation to the scanner can be determined by the control computer with the use of the environmental parameter and the at least one field map.

Furthermore, the travel mechanism can be controlled by the control computer depending on the at least one field map. In particular, with the use of the field map and the environmental parameters, which are preferably determined continuously, both the distance from the patient support device and the direction of the patient support device in relation to the scanner can be ascertained. With this information, for example, the speed or a further direction of movement of the patient support device can subsequently be determined by the control computer, and the travel mechanism can then be activated appropriately.

Furthermore, a threshold value of the environmental parameter can be adjustable in the control computer, the threshold value specifying a criterion for the environmental parameter in order to ascertain a control parameter for controlling the travel mechanism by the control computer. The threshold value is preferably entered manually into the control computer by a user via a user interface. With the threshold value, it is possible to prevent the control computer from activating the travel mechanism too early, such as when the patient support device is still outside an examination room and there is therefore a wall between the patient support device and the scanner. By entering or specifying the threshold value, a high level of safety can be advantageously achieved when transporting the patient support device. In particular, the threshold value designates a lower limit for the relevant environmental parameter, and at least partially automatic control of the travel mechanism by the control computer can occur only when the threshold value is reached or exceeded by the detected environmental parameter.

In another embodiment of the invention, the travel mechanism is automatically controlled with the use of the ascertained control parameter by the control computer as soon as the control parameter is ascertained. The user is thus advantageously assisted in real time hereby when moving and/or operating the patient support device. In particular, the user can be assisted during a docking procedure in which an exact position of the patient support device in relation to the scanner is necessary. During the docking procedure, the patient support device is located in the magnetic field of the basic field magnet of the scanner, so that the docking procedure can be controlled as a function of the detected environmental parameter. Preferably, the user is also shown that the travel mechanism is automatically controlled by the control computer so that the user can attend to further activities during this time, i.e., during the docking procedure. In addition, an advantageous saving of time can be achieved for the user by the automatic control of the travel mechanism by the control computer when preparing a magnetic resonance scan.

Alternatively or in addition, with the use of the ascertained control parameter, the travel mechanism can be automatically controlled by the control computer in response to a user action. This enables advantageous support of the user when moving the patient support device, whereby the user retains control of management by the user action. For example, this can occur as a result of the user pressing a "Forwards" button or by pressing a "Dock-On" button or further buttons that are considered appropriate to those skilled in the art.

Furthermore the height of the bed can be determined with the use of the environmental parameter by the control computer. This has the advantage that the position or location of the bed in the area can be determined. In addition, the bed of the patient support device may already be adjusted to a requisite height for the docking procedure before docking with the scanner. An interruption of the docking procedure to move the bed of the patient support device to the requisite height thus can be omitted. Preferably a requisite height for the docking procedure is automatically set by the control computer by the ascertained or determined height of the bed on the patient support device.

It is also possible for the control computer to use the environmental parameter in order to identify the type of the basic field magnet of the scanner to which docking will occur. With the use of the type of magnet, the occurrence of a spatial change of the magnetic field, in particular outside the scanner, can be ascertained. The spatial change of the magnetic field, in particular outside the scanner, may depend on the type of magnet. With the spatial change of the magnetic field as the detected environmental parameter, a particularly simple determination of the position or the direction of movement of the patient support device can be achieved. The environmental parameter is preferably compared with field maps stored in the control computer so as to determine the type of magnet.

The present invention also encompasses a non-transitory, computer-readable data storage medium that is loadable into a control computer of a patient support device. The storage medium is encoded with programming instructions that cause the patient support device, when executed by the control computer, to implement any or all of the embodiments of the method and device according to the invention, as described above.

The computer code may require program support, e.g. libraries and auxiliary functions, to realize the corresponding embodiments of the method. The code may be software with a source code that has still to be compiled and linked or only interpreted, or an executable software code that only remains to be loaded into a corresponding arithmetic unit for execution.

DESCRIPTION OF THE PREFERRED EMBODIMENTS

Figure 1:
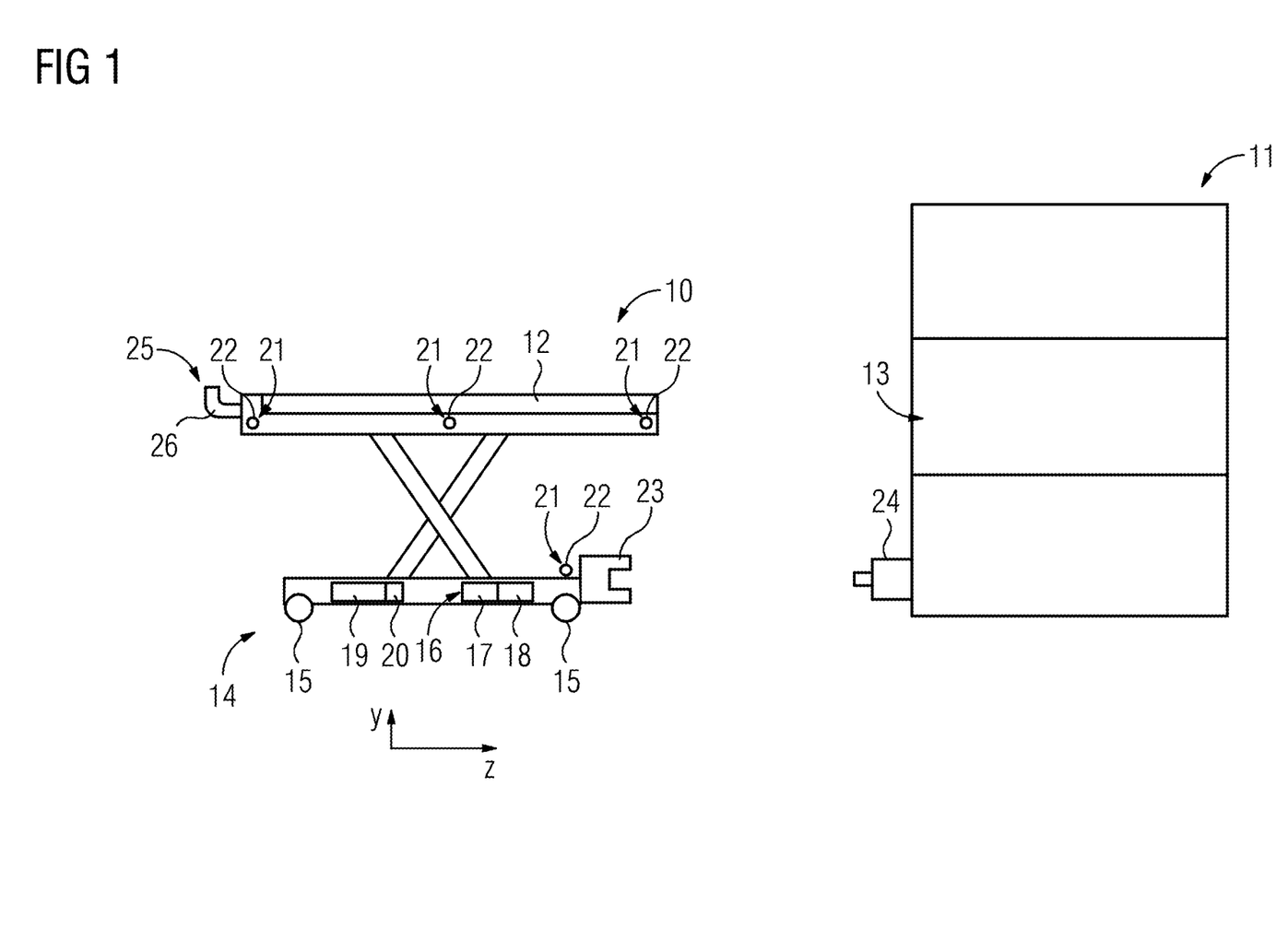
FIG. 1 shows a patient support device according to the invention and a magnetic resonance scanner, in a schematic side view.
Figure 2:
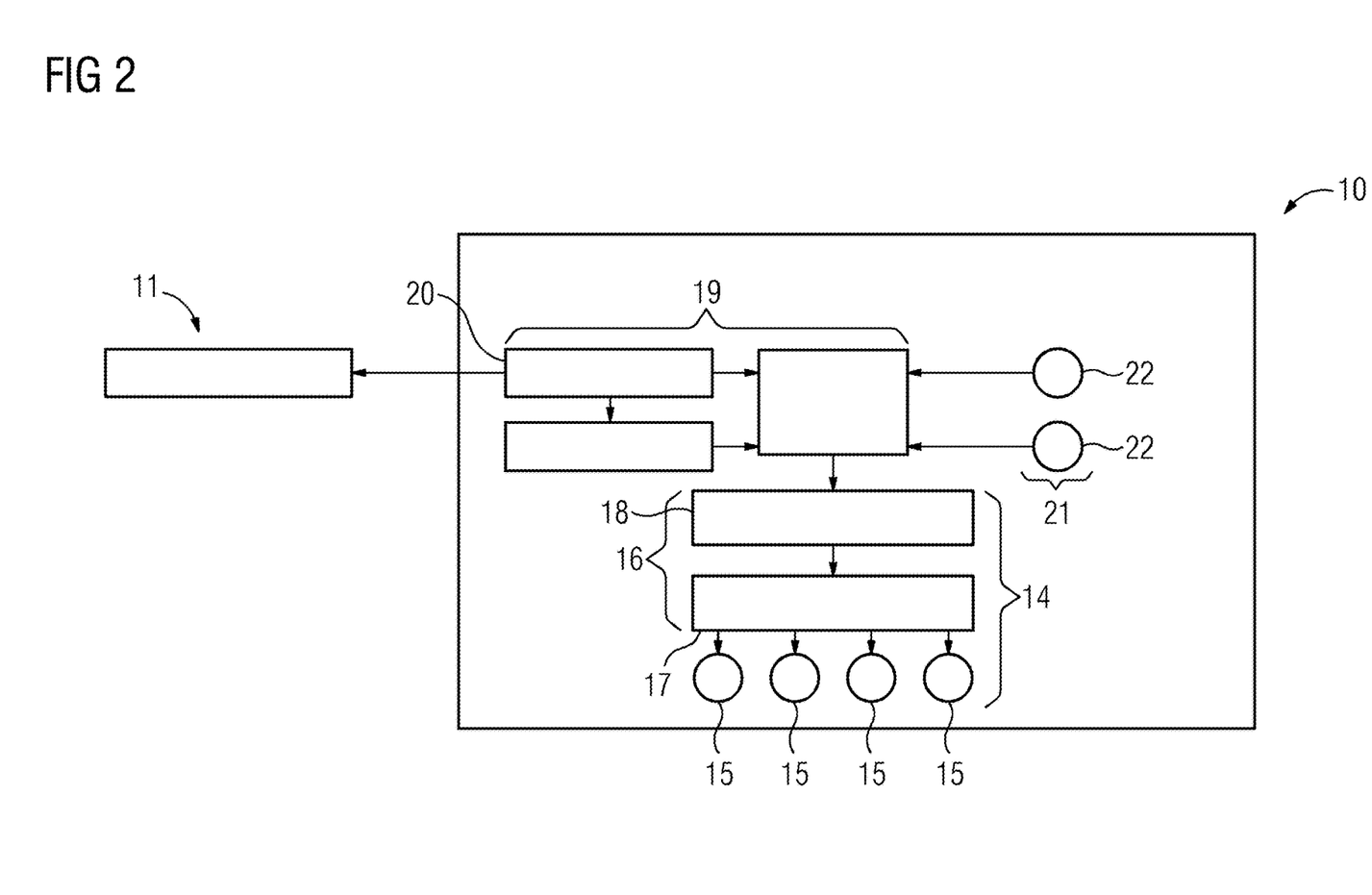
FIG. 2 is a block diagram of the patient support device and the magnetic resonance scanner.
Figure 3:
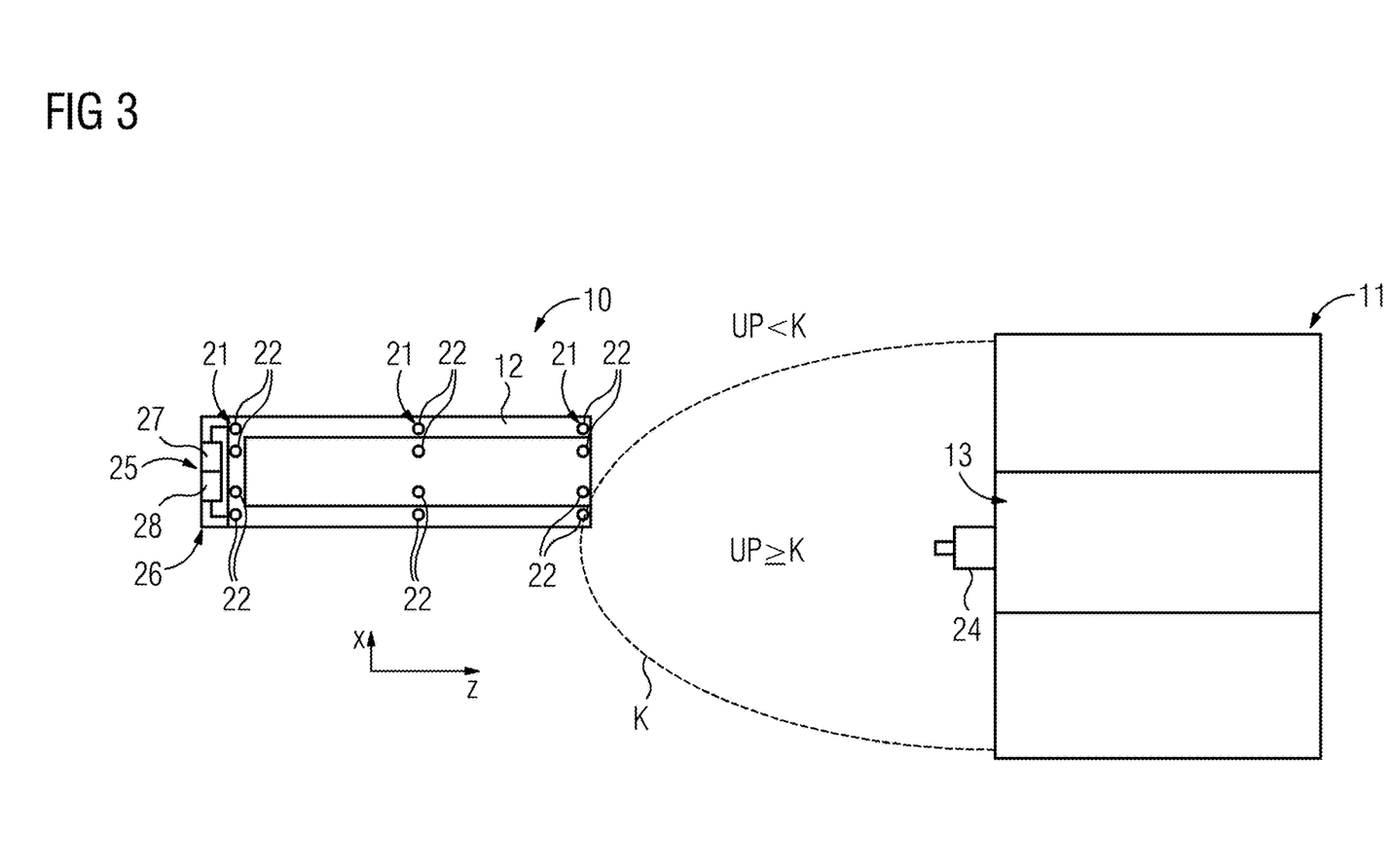
FIG. 3 shows the patient support device and the magnetic resonance scanner in a schematic top view.

In FIGS. 1 to 3 schematic views of a patient support device 10 according to the invention and a magnetic resonance scanner 11 are shown. The patient support device 10 comprises a bed 12 that can be moved inside a patient reception area 13 of the scanner 11 as soon as the patient support device 10 is docked with the scanner 11.

The patient support device 10 also has a travel mechanism 14 (FIGS. 1 and 2), which faces away from the bed 12 on the patient support device 10. The travel mechanism 14 is designed to move the patient support device 10 and has a number of rolling elements (rolling bodies) 15. In FIG. 1, only two of the rolling elements 15 can be seen. The travel mechanism preferably has four or five rolling elements 15. The individual rolling elements 15 are formed by wheels.

Furthermore, the travel mechanism 14 also has a drive 16 with a motor 17 and a motor driver 18 (FIG. 2). The motor 17 is actuated by the motor driver 18. The motor 17 generates a drive torque by which the individual rolling elements 15 of the travel mechanism 14 are rotated. The individual rolling elements 15 are preferably activated individually by the motor 17.

Furthermore, the patient support device 10 has a control computer 19 (FIGS. 1 and 2). The travel mechanism 14, in particular, the motor driver 18 and the motor 17, are controlled by the control computer 19. The control computer 19 has a central control processor by which a height adjustment unit for the bed 12 can also be activated. The control computer 19 has a communication interface 20 for communication with the scanner 11. The communication interface 20 is preferably cable-free or wireless in design. In the present exemplary embodiment, the communication interface 20 comprises a radio connection with the scanner 11. Different embodiments of the communication interface 20 for communication between the control computer 19 of the patient support device 10 and the scanner 11 are conceivable in alternative embodiments of the invention.

The patient support device 10 has a sensor 21 for detecting at least one environmental parameter UP of the patient support device 10 (FIGS. 1 to 3). The sensor 21 has a number of environmental sensors that, in the present exemplary embodiment, are each formed as a $B_0$ field sensor 22. The individual $B_0$ field sensors 22 are preferably each a Hall effect sensor. The individual $B_0$ field sensors 22 are each designed to detect an environmental parameter UP of the patient support device 10. In particular, the individual $B_0$ field sensors 22 are designed to detect a value of a $B_0$ field of the scanner 11 or a magnetic field strength thereof at the location of the patient support device. The individual $B_0$ field sensors 22 are distributed on the patient support device 10. The individual $B_0$ field sensors 22 are preferably arranged in a front area of the patient support device 10 or on the bed 12 of the patient support device 10. The multiple $B_0$ field sensors 22 are also arranged at a distance from one another so that a high degree of accuracy and clarity of the detected environmental parameter UP can be achieved.

In an alternative embodiment of the invention, the individual environmental sensors may also include a magnetic field sensor that detects a gradient field and/or to detect the $B_1$ field. The individual environmental sensors detect light markings in a further embodiment of the invention. In the present embodiment, however, the invention is described in an exemplary manner with the embodiment of the individual environmental sensors as $B_0$ field sensors 22, in particular, Hall effect sensors. Embodiments of the patient support device with the environmental sensors being magnetic field sensors for detecting a gradient field and/or the $B_1$ field, and/or being sensors as sensors for detecting light markings, operate analogously to the embodiment of the environmental sensors as $B_0$ field sensors 22.

A docking unit 23 is arranged in the front area of the patient support device 10 that conforms to a docking unit 24 of the scanner 11. The docking unit 23 of the patient support device 10 is designed, together with the docking unit 24 of the scanner 11, to enable docking of the patient support device 10 with the scanner 11. At least one of the $B_0$ field sensors 22 (or multipole $B_0$ field sensors 22) are arranged in this front area in close proximity to the docking unit 23 of the patient support device 10, In FIG. 1 only a single $B_0$ field sensor 22 can be seen. The bed 12 of the patient support device 10 also has a number of $B_0$ field sensors 22, which are distributed on the bed 12. The $B_0$ field sensors 22 are arranged in a front area of the bed 12 and/or in an edge area of the bed 12. For example, the $B_0$ field sensors 22 are distributed around the surface of the bed 12 on which the patient reclines.

Moreover, the patient support device 10 has a user interface 25 arranged in a handle area 26 of the patient support device 10 (FIGS. 1 and 3). The user interface 25 preferably has an input unit 27 via which the user can activate inputs for the operation of the patient support device 10. The user interface 25 also has an output unit 28 for transmitting information from the patient support device 10 to the user.

The detected environmental parameters UP represent a magnetic field strength and/or a value of the $B_0$ field, which is the basic magnetic field generated by the basic magnet of the scanner 11, at the location of the patient support device 10. At least one control parameter is ascertained by the control computer 19 with the use of the detected environmental parameter UP, and the travel mechanism 14 is controlled by the ascertained control parameter. The control computer 19 is designed so that first a position of the patient support device 10 in relation to the scanner 11 is ascertained with the use of the detected environmental parameter UP. Furthermore, based on the position of the patient support device 10, the control computer 19 is designed to generate the control parameter with which the travel mechanism 14, in particular the drive 16 of the travel mechanism 14, is activated.

In addition, a threshold value K for the environmental parameter UP can be adjusted and/or entered by a user via the user interface 25. The threshold value K specifies a criterion for the environmental parameter UP for determining the control parameter for controlling the travel mechanism 14 by the control computer 19. The criterion of the environmental parameter UP specifies a lower limit for the environmental parameter UP from which the at least one control parameter is determined as a function of the environmental parameter UP. For example, the criterion can be a lower limit for a value of the magnetic field strength (FIG. 3). If the environmental parameter UP is below the selected and/or adjusted criterion, that is to say, below the lower limit for the detected environmental parameter UP, the control computer 19 does not determine a control parameter as a function of that environmental parameter UP. On the other hand, if the detected environmental parameter UP is greater than or equal to the selected or adjusted criterion, that is to say, greater than or equal to the lower limit for the detected environmental parameter UP, the control computer 19 then determines a control parameter as a function of the environmental parameter UP.

Figure 4:
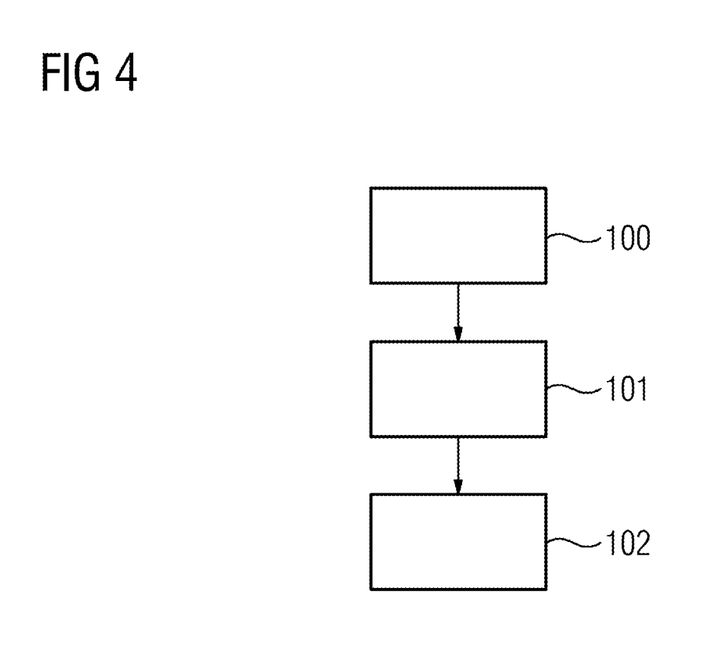
FIG. 4 is a flowchart of the method according to the invention for controlling the travel mechanism of the patient support device.

FIG. 4 shows a method for controlling the travel mechanism 14 of the patient support device 10 by the control computer 19. The control computer 19 has computer programs and/or software to control the travel mechanism 14, which can be loaded directly into a memory, with program code to execute the method for controlling the travel mechanism 14 of the patient support device 10 when the computer programs and/or software are executed in the control computer 19. The control computer 19 has a processor designed to execute the computer programs and/or software, and can also include the memory.

The software or computer programs are stored on an electronically readable data carrier separate from the control computer 19 so as to be loadable into the aforementioned memory.

The method for controlling the travel mechanism 14 of the patient support device 10 by the control computer 19 is described in an exemplary manner in the context of the embodiment of the individual environmental sensors as $B_0$ field sensors 22, in particular, Hall effect sensors. The method for controlling the travel mechanism 14 of the patient support device 10 by the control computer 19 is executed analogously in alternative embodiments of the environmental sensors as magnetic field sensors for detecting a gradient field and/or the $B_1$ field, and/or the environmental sensors as sensors for detecting light markings.

In a first method step 100 of the method, at least one environmental parameter UP of the patient support device 10 is first detected by the sensor 21. The individual $B_0$ field sensors 22 of the sensor 21 each detect an environmental parameter UP, in particular, a value of a $B_0$ field, at the location of the patient support device 10. The environmental parameters UP detected by the individual $B_0$ field sensors 22 are also dependent on the position of the patient support device 10 in relation to the scanner 11. If the patient support device 10 is at a short distance of, for example, 1 m to 2 m from the scanner 11, in particular, in a front area or a rear area of the scanner 11, the individual $B_0$ field sensors 22 are also at a short distance from the scanner 11 and thus detect the environmental parameter UP with a high value of the magnetic field strength and/or a high $B_0$ field. If the patient support device 10 is at a great distance from the scanner 11, the individual $B_0$ field sensors 22 are therefore also at a great distance from the scanner 11 and thus detect the environmental parameter UP with a low value of the magnetic field strength and/or a small $B_0$ field.

In a subsequent method step 101, a control parameter for activating the travel mechanism 14 is ascertained by the control computer 19 as a function of the at least one detected environmental parameter UP, in particular, as a function of the multiple detected environmental parameters UP. In addition, in this method step 101 a threshold value K can be entered by a user in order to determine the control parameter, via the input unit 27 of the user interface 25. The threshold value K specifies a criterion for the environmental parameter UP for determining the control parameter for controlling the travel mechanism 14. A user can therefore establish a value of the magnetic field strength by the threshold value K, from which a control parameter for controlling the travel mechanism 14 is determined by the control computer 19. Thus, the control parameter for controlling the travel mechanism 14 is determined only if and when a detected environmental parameter UP is equal to the threshold value K or greater than the threshold value K. Conversely, if a detected environmental parameter UP is smaller than the threshold value K, a control parameter for controlling the travel mechanism 14 is not determined for this environmental parameter UP. It is therefore possible for the user to establish when a start of assistance is desired while moving the patient support device 10.

In addition, the threshold value K may already be preset with a lower limit so that a user can only enter an upwardly variable threshold value K. Such a default setting of the threshold value K may be useful in preventing automatic and/or independent control of the travel mechanism 14 by the control computer 19 while still outside the examination room in which the scanner 11 is situated.

In this method step 101 of ascertaining at least one control parameter, inasmuch as the detected environmental parameters UP are greater than the threshold value K, a position of the patient support device 10 in relation to the scanner 11 is first ascertained with the use of the detected environmental parameter UP. The environmental parameters UP detected by the individual $B_0$ field sensors 22 are compared with field maps, in particular, magnetic field maps, deposited or stored in the control computer 19. Inside the control computer 19, in particular inside the memory of the control computer 19, a number of field maps can be stored respectively for various types of the basic field magnet of various scanners 11. By comparing the detected environmental parameter UP with the individual field maps, the field map that most closely matches the (preferably) multiple environmental parameters UP is selected. On the basis of the $B_0$ field sensors 22 distributed on the patient support device 10, a spatial distribution of the detected environmental parameters UP can be compared to the field maps, and the field map that most closely matches the multiple environmental parameters UP is selected.

With the use of the selected field map and the detected environmental parameters UP, the position of the patient support device 10 in relation to the scanner 11 can be determined by the control computer 19. In addition, a direction of movement and/or orientation of the patient support device 10 in relation to the scanner 11 can be determined with the use of the selected field map and the detected environmental parameters UP. By selecting a field map, a magnet type and/or a design of magnet of the scanner 11 can also be determined.

Furthermore, in this method step 101 of ascertaining at least one control parameter, a field map can also be selected by a communication of the control computer 19 of the patient support device 10 with the scanner 11. Information can be exchanged with the scanner 11, for example, via the communication interface 20 of the control computer 19, and information from a field map and/or a field distribution of the magnet of the scanner 11 can be transmitted to the control computer 19.

In addition, in a further embodiment of the invention, the field map selected by the control computer 19 can be used in establishing the threshold value K for the environmental parameter UP. The threshold value K can be given a default setting and/or a presetting by the control computer 19 dependent on the selected field map.

With the use of the ascertained distance and/or the ascertained orientation of the patient support device 10 in relation to the scanner 11 and the selected field map, at least one control parameter is generated by the control computer 19 for activating the travel mechanism 14. The control parameter may designate control information for activating the drive 16. In order to activate the drive 16 the control parameter may designate control information as to a speed to be set and/or control information of a direction of movement of the rolling elements 15 to be set.

In the method step 101 of ascertaining at least one control parameter, the height of the bed 12 can also be determined by the control computer 19. This information can be obtained with the use of the detected environmental parameter UP of the $B_0$ field sensor 22 inside the bed 12.

In a further method step 102, the travel mechanism 14 is activated by the control computer 19 with the use of the at least one ascertained and generated control parameter. The travel mechanism 14, in particular, the drive 16, can be controlled completely automatically by the control computer 19 with the use of the at least one control parameter, once a control parameter is ascertained and generated by the control computer 19. This enables essentially automatic navigation of the patient support device 10 in the vicinity of the scanner 11 without necessitating user action. Automatic and/or independent navigation for a docking procedure of the patient support device 10 with the scanner 11 can be provided in this manner. The control parameters for activating the travel mechanism 14 are designed such that exact positioning of the patient support device 10 for the docking procedure with the scanner 11 is achieved.

Once automatic navigation of the patient support device 10 is controlled by the control computer 19 with the use of the ascertained and generated control parameter, output information is also generated by the control computer 19. This output information is conveyed via the user interface 25, namely the output unit 28 of the user interface 25, to the user so that the user can make use of the time of automatic navigation and/or automatic docking of the patient support device 10 by the control computer 19 for further activities.

Alternatively or in addition, in this further method step 102 of activating the travel mechanism 14 by the control computer 19 with the use of the at least one ascertained and generated control parameter, the travel mechanism 14, in particular the drive 16, may be only partially automatically controlled by the control computer 19 with the use of the at least one control parameter. This requires a user action by the user via the user interface 25, namely the input unit 27 of the user interface 25. For example, the user may press and/or keep pressing a button such as a "Forwards" button, a "Dock-On" button, etc. The further navigation procedure and/or docking procedure, however, is performed automatically and/or spontaneously by the control computer 19 with the use of the ascertained and/or generated control parameter.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A patient support device comprising:
   a bed adapted to receive a subject thereon;
   a movable device structure;
   a travel mechanism in driving connection with the movable device structure, said travel mechanism being configured to move the device structure according to a control parameter provided to the travel mechanism;
   a control computer;
   a sensor in communication with said control computer, said sensor detecting at least one environmental parameter of a combination of the bed and the travel mechanism; and
   said control computer being configured to generate said control parameter dependent on the environmental parameter detected by said sensor, and to provide the determined control parameter to the travel mechanism,
   wherein said sensor comprises at least one environmental sensor that comprises a $B_0$ field sensor designed to detect a value of a $B_0$ field of a scanner, said patient support device has a front region at which a device docking unit is situated, said device docking unit being configured to dock with a docking unit of said scanner, and said senor is arranged in the front region.

2. A patient support device as claimed in claim 1 wherein said one $B_0$ field sensor is a Hall effect sensor.

3. A patient support device as claimed in claim 1 wherein said sensor comprises two environmental sensors situated at a distance from each other.

4. A patient support device as claimed in claim 1 wherein said sensor comprises at least one environmental sensor situated inside said bed.

5. A patient support device as claimed in claim 1 comprising a user interface in communication with said control computer, said user interface being configured to receive a manually entered threshold value for said environmental parameter, and wherein said control computer is configured to determine said control parameter only when said environmental parameter is equal to or above said threshold value.

6. A patient support device as claimed in claim 1 wherein said patient support device is used in combination with a magnetic resonance scanner, and wherein said control computer comprises a communication interface for communication with said magnetic resonance scanner.

7. A magnetic resonance apparatus having a patient support device comprising:
   a bed adapted to receive a subject thereon;
   a movable device structure;
   a travel mechanism in driving connection with the movable device structure, said travel mechanism being configured to move the device structure according to a control parameter provided to the travel mechanism;
   a control computer;
   a sensor in communication with said control computer, said sensor detecting at least one environmental parameter of a combination of the bed and the travel mechanism; and
   said control computer being configured to generate said control parameter dependent on the environmental parameter detected by said sensor, and to provide the determined control parameter to the travel mechanism,
   wherein said sensor comprises at least one environmental sensor that comprises a $B_0$ field sensor designed to detect a value of a $B_0$ field of a scanner, said patient support device has a front region at which a device docking unit is situated, said device docking unit being configured to dock with a docking unit of said scanner, and said sensor is arranged in the front region.

8. A method for controlling movement of a movable patient support device comprising:
   detecting at least one environmental parameter comprising at least one of a value of a $B_0$ field of the patient support device with a sensor attached to the patient support device, wherein the sensor comprises at least one environmental sensor that comprises a $B_0$ filed sensor designed to detect a value of a $B_0$ field of a scanner;
   providing said at least one environmental parameter detected by said sensor to a computer and, in said computer, determining at least one control parameter for a travel unit that imparts movement to said patient support device;
   in said computer, accessing a field map that represents a spatial distribution of at least one of said $B_0$ field, and wherein said computer is configured to identify a position of said patient support device relative to said scanner from said at least one environmental parameter and said field map, and to generate said at least one control parameter dependent on said position; and
   providing said at least one control parameter to said travel unit from said computer in order to move said patient support device according to said at least one control parameter.

9. A method as claimed in claim 8 comprising moving said patient support device relative to a magnetic resonance scanner in which a gradient field is produced, and in which a radio-frequency field ($B_1$ field) is produced, and a plurality of light markings are produced, and wherein said sensor detects said environmental parameter as, a value of said gradient field, a value of $B_1$ field, and a number of said plurality of light markings.

10. A method as claimed in claim 9 wherein said computer is configured to identify a type of magnet of said scanner from said environmental parameter.

11. A method as claimed in claim 8 comprising generating said at least one control parameter dependent on said position so as to operate the travel unit to move the patient support device relative to the scanner.

12. A method as claimed in claim 8 wherein said computer is configured to identify a type of magnet of said scanner by comparing said environmental parameter with said field map.

13. A method as claimed in claim 8 comprising setting a threshold value in said computer of said environmental parameter, and, in said computer, determining said control parameter only when said environmental parameter equal or exceeds said threshold value.

14. A method as claimed in claim 8 comprising automatically moving said patient support device with said travel unit automatically controlled, with said control parameter, from said computer.

15. A method as claimed in claim 8 comprising moving said patient support device by a combination of automatic movement imparted by said travel unit controlled by said computer with said at least one control parameter, and user action manually applied to said patient support device.

16. A method as claimed in claim 8 comprising, in said computer, determining a height of said patient support device from said environmental parameter.

17. A method as claimed in claim 8 comprising, from said environmental parameter, determining, in said computer, a direction of movement to be imparted to said patient support device and generating said control parameter to cause said patient support device to be moved by said travel unit in said direction of movement.

18. A non-transitory, computer-readable data storage medium encoded with programming instructions for controlling movement of a movable patient support device comprising a sensor, a travel unit, and a computer, said storage medium being loaded into said computer and said programming instructions causing said computer to:

receive at least one environmental parameter comprising at least one of a value of a $B_0$ field of a scanner detected by said sensor attached to the patient support device, wherein the sensor comprises at least one environmental sensor that comprises a $B_0$ field sensor;

determine at least one control parameter for the travel unit in order to impart movement to said patient support device;

access a field map that represents a spatial distribution of at least one of said $B_0$ field, and wherein said computer is configured to identify a position of said patient support device relative to said scanner from said at least one environmental parameter and said field map, and to generate said control parameter dependent on said position; and provide said at least one control parameter to said travel unit from said computer in order to move said patient support device according to said control parameter.

* * * * *